US010758163B2

(12) United States Patent
Teissier et al.

(10) Patent No.: US 10,758,163 B2
(45) Date of Patent: Sep. 1, 2020

(54) ASSISTANCE DEVICE INTENDED FOR A PERSON SUFFERING MOTOR DISORDERS OF NEUROLOGICAL ORIGIN

(71) Applicant: RESILIENT INNOVATION, Montpellier (FR)

(72) Inventors: Sébastien Teissier, Montpellier (FR); Jordan Miron, Servies en Val (FR)

(73) Assignee: RESILIENT INNOVATION, Montpellier (FR)

( * ) Notice: Subject to any disclaimer, the term of this patent is extended or adjusted under 35 U.S.C. 154(b) by 214 days.

(21) Appl. No.: 15/555,235

(22) PCT Filed: Mar. 3, 2016

(86) PCT No.: PCT/FR2016/050488
§ 371 (c)(1),
(2) Date: Sep. 1, 2017

(87) PCT Pub. No.: WO2016/139428
PCT Pub. Date: Sep. 9, 2016

(65) Prior Publication Data
US 2018/0344211 A1 Dec. 6, 2018

(30) Foreign Application Priority Data

Mar. 3, 2015 (FR) .................................... 15 51771

(51) Int. Cl.
*A61B 5/00* (2006.01)
*A61B 5/11* (2006.01)
*A61B 5/024* (2006.01)

(52) U.S. Cl.
CPC .............. *A61B 5/112* (2013.01); *A61B 5/024* (2013.01); *A61B 5/1101* (2013.01);
(Continued)

(58) Field of Classification Search
CPC ... A61B 5/1101; A61B 5/1116; A61B 5/1117; A61B 5/112; A61B 5/024; A61B 5/486
See application file for complete search history.

(56) References Cited

U.S. PATENT DOCUMENTS

| 9,591,993 B2 * | 3/2017 | Morris Bamberg ........................ A61B 5/1038 |
| 2009/0043531 A1 * | 2/2009 | Kahn .................... G16H 40/63 702/149 |

(Continued)

FOREIGN PATENT DOCUMENTS

WO WO 2009/083032 A1 7/2009

OTHER PUBLICATIONS

Cha et al., "Immediate Effects of Rhythmic Auditory Stimulation with Tempo Changes on Gait in Stroke Patients," J. Phys. Ther. Sci., vol. 26, 2014, pp. 479-482.

(Continued)

*Primary Examiner* — Max F Hindenburg
(74) *Attorney, Agent, or Firm* — Arent Fox LLP (57) ABSTRACT

The invention relates to an assistance device intended for a person (1) suffering from motor disorders of neurological origin, comprising:
  an accelerometer suitable for being worn by the person to measure accelerations; and
  storage means storing a plurality of previously defined alert acceleration threshold values; and
  means (5) for emitting an auditory stimulation perceptible to the person wearing the accelerometer; and
calculation means configured to perform the following steps:
  a) determine a posture of the person from the measured accelerations;
  b) compare the accelerations measured by said accelerometer in the first direction in relation to at least one anticipatory acceleration threshold value associated with said posture;

(Continued)

c) command the emission of an auditory stimulation as a function of the crossing of said anticipatory acceleration threshold value associated with said posture for a determined time associated with said anticipatory acceleration threshold value.

15 Claims, 2 Drawing Sheets

(52) U.S. Cl.
CPC ............ *A61B 5/1116* (2013.01); *A61B 5/486* (2013.01); *A61B 5/7405* (2013.01); *A61B 2560/0223* (2013.01); *A61B 2560/0228* (2013.01); *A61B 2562/0219* (2013.01)

(56) References Cited

U.S. PATENT DOCUMENTS

| | | |
|---|---|---|
| 2009/0204030 A1 | 8/2009 | Brauers et al. |
| 2010/0274304 A1* | 10/2010 | Wang .................... A61B 5/112 607/3 |
| 2012/0101411 A1 | 4/2012 | Hausdorff et al. |
| 2012/0184878 A1* | 7/2012 | Najafi ................... A61B 5/112 600/592 |
| 2012/0259255 A1* | 10/2012 | Tomlinson ............... A61H 3/00 601/46 |
| 2014/0372045 A1 | 12/2014 | Keski-Pukkila et al. |

OTHER PUBLICATIONS

Hausdorff et al., "Rhythmic auditory stimulation modulates gait variability in Parkinson's disease," European Journal of Neuroscience, vol. 26, 2007, pp. 2369-2375.

International Search Report issued in International Application No. PCT/FR2016/050488, dated May 12, 2016 (3 pages).

Rossignol et al., "Audio-Spinal Influence in Man Studied by the H-Reflex and its possible Role on Rhythmic Movements Synchronized to Sound," Electroencephalography and Clinical Neurophysiology, vol. 41, 1976, pp. 83-92.

Spaulding et al., "Cueing and Gait Improvement Among People with Parkinson's Disease: A Meta-Analysis," Archives of Physical Medicine and Rehabilitation, vol. 94, 2013, pp. 562-570.

Thaut et al., "Rhythmic Auditory Stimulation in Rehabilitation of Movement Disorders: A Review of Current Research," Music Perception, vol. 27, 2009, pp. 263-269.

* cited by examiner

FIG 1

ASSISTANCE DEVICE INTENDED FOR A PERSON SUFFERING MOTOR DISORDERS OF NEUROLOGICAL ORIGIN

CROSS REFERENCE TO RELATED APPLICATIONS

This application is a 35 U.S.C. 371 National Phase of PCT Application No. PCT/FR2016/050488 filed Mar. 3, 2016, which claims benefit to FR Application No. 1551771 filed Mar. 3, 2015, the disclosure of which is hereby incorporated by reference in its entirety.

TECHNICAL FIELD OF THE INVENTION AND CONTEXT

The present invention relates to a mobility assistance device intended for people suffering from motor disorders of neurological origin, in particular those due to a neurodegenerative disease such as Parkinson's disease. The expression "motor disorders" should be understood to mean a loss of control by the user, partial or total, of the muscles enabling him or her to move around. These motor disorders are likely to prevent this person from walking or make him or her fall. More specifically, the present application relates to an assistance device that makes it possible to trigger an auditory stimulation of the user wearing said device, when an episode of motor disorders risks occurring or does indeed occur, in order to enable him or her to prevent the occurrence thereof.

The expression "neurological origin" should be understood to mean the fact that the motor disorders are caused by an impairment, in the affected person, of the nervous system, rather than by osteo-articular or muscular disorders. The neurodegenerative diseases are generally the cause of this impairment, and the invention addresses in particular the people who are affected by them, and notably including idiopathic Parkinson's disease, parkinsonian syndromes, multisystem atrophy, Lewy body dementia, or progressive supranuclear palsy, among others. Other diseases such as multiple sclerosis can be involved, as can incidental impairments such as the consequences of a cerebral vascular incident or of a transient ischemic incident. The following description will refer to idiopathic Parkinson's disease as nonlimiting illustrative example.

Idiopathic Parkinson's disease is the second neurodegenerative pathology after Alzheimer's disease. The age of occurrence of the disease is located between 58 and 62 years and more rarely (in less than 10% of the cases) before 40 years. This pathology is characterized by an impairment of the operation of the system of basal ganglia (putamen, globus pallidus, locus niger and the subthalamic nucleus). The basal ganglia are subcortical nuclei in the brain forming part of a motor circuit (including the thalamus, motor cortex, and prefrontal cortex) responsible above all for controlling deliberate movements. In idiopathic Parkinson's disease a depopulation of the dopaminergic neurons of the locus niger which are related to the striatum is observed (affecting the nigro-striated bundles). The nigro-striated affect leads to a reduction of the activation of the thalamus which leads to difficulties in initiating deliberate movements. For many years, Parkinson's disease has been considered purely as a pathology of motricity characterized by the "parkinsonian triad". This comprises three symptoms which are tremor at rest, muscular rigidity and akinesia. At the start of Parkinson's disease, the symptomatology is conventionally unilateral to then become bilateral, while still remaining asymmetrical.

The parkinsonian triad generates motor disorders which, when associated with postural instability, generate gait disorders and falls often causing injury (fractures of the neck of the femur, cranial injuries). The dopamine deficit at the nigro-striated level would partly explain these motor disorders. The normal elderly subject shows gait impairment, reduced gait speed, reduced step length, increased step frequency and step asymmetry and variability. In a subject suffering parkinsonian syndrome, these deficits are much more marked. The gait disorders also include freezing or freezing of gait. This is a gait disorder defined as a reduction of the progress of the step despite an intention on the part of the subject to want to advance, which generally leads to a total stop of the subject suffering from Parkinson's disease, despite this intention to want to advance. Freezing of gait occurs in a vast majority of the patients at an advanced stage.

Freezing of gait manifests upon the initiation of gait (above all after rising from the chair or the bed or after prolonged immobilization) or during gait promoted by the situation of double-tasking including mental calculation, by stress, narrow passages, and door passageways. Freezing of gait, or "freezing", is characterized by an increase in gait frequency, associated with a reduction of the length of the strides, but also by the sensation of feet being "magnetized to the ground". This freezing phenomenon is one of the most incapacitating symptoms of Parkinson's disease significantly affecting the quality of life of the patients.

The freezing phenomenon can be mitigated or avoided by making a patient listen to a rhythmic pulsing. More specifically, it consists in the presentation of rhythmic auditory indices (for example the sounds of a metronome or of music), in order to help the patient walk better by enabling him or her to regularize, stabilize his or her movements, through the synchronization of the movements of his or her limbs with music for example.

The document US 2010/0274304 A1 describes an example of a type of device, placed on a shoe of the user and emitting a signal when the device detects an irregularity in the step pace. More specifically, the signal is emitted from the moment when the user stops advancing. The signal emitted is then transformed into an auditory signal by a transcriber placed at the level of the ear of the user, to allow him or her to begin walking again. In other words, this device allows the user to reinitialize his or her gait after the latter was interrupted by a freezing phenomenon. However, such a detection is imperfect, because the change of rate of the walker can be caused by various factors other than freezing. The result thereof is an unwanted triggering of the auditory stimulus, which becomes a nuisance and dissuades the person from using the device.

There is a need for a motricity assistance device that makes it possible to prevent the occurrence of a phenomenon of freezing of the gait of a user wearing said device and making it possible to detect, early, a phenomenon of freezing of the gait of the user wearing said device, in order to allow him or her to restore a normal gait, but avoiding an unwanted triggering of the device in the absence of freezing.

SUMMARY OF THE INVENTION

The aim of the invention is to at least partly remedy these drawbacks and preferentially remedy all drawbacks, by proposing a motricity assistance device intended for a person suffering from motor disorders of neurological origin in order for it to make it possible to avoid the occurrence of freezing, and, in the case of freezing, to detect its occurrence as quickly as possible, without false-positive, and which makes it possible to auditorily stimulate this person for him or her to restore an acceptable motricity.

An assistance device is thus proposed that is intended for a person suffering from motor disorders of neurological origin, comprising:
- an accelerometer suitable to be worn by the person to measure accelerations in at least one first direction; and
- storage means storing a plurality of prevention acceleration threshold values previously defined for said first direction; and
- means for emitting an auditory stimulation perceptible to the person wearing the accelerometer; and
- calculation means connected to the accelerometer, to the storage means and to the emission means;

the assistance device is characterized in that the first direction corresponds to the horizontal axis, and in that the calculation means are configured to:
- a) determine a posture of the person based on the measured accelerations,
- b) compare the accelerations measured by the inertial unit in the first direction in relation to at least one anticipatory acceleration threshold value associated with said posture;
- c) command the emission of an auditory stimulation as a function of the crossing of said anticipatory acceleration threshold value associated with said posture for a predetermined time associated with said anticipatory acceleration threshold value.

This device is advantageously completed by the following features, taken alone or in any of the technically possible combinations thereof:
- the determined time associated with said anticipatory acceleration threshold value is a function of the direction of crossing of said anticipatory acceleration threshold value by the measured accelerations;
- the postures comprise the seated-recumbent posture, and an anticipatory acceleration threshold value associated with the seated-recumbent posture corresponds to a backward imbalance;
- the postures comprise the standing posture, an anticipatory acceleration threshold value associated with the standing posture corresponding to a backward imbalance and an anticipatory acceleration threshold value associated with the standing posture corresponding to a forward movement;
- the device comprises an inertial unit of which the accelerometer forms part, said inertial unit being also configured to determine an orientation of the trunk of the person, said orientation being used to determine the posture of the person;
- the accelerometer is also adapted to measure accelerations in a second direction, said second direction corresponding to the vertical, and the storage means store at least one alert acceleration threshold value previously defined in a second direction, the calculation means being also configured to:
  - a) compare the accelerations measured by the inertial unit in the second direction,
  - b) generate an alert signal when a measured acceleration has a value above the alert acceleration threshold value,
  - c) command the emission means to emit an auditory stimulation as a function of the alert signal;
- the storage means store a time threshold value and a gait acceleration threshold value, and the calculation means are configured to measure a time interval between two acceleration measurements exceeding said gait acceleration threshold value and trigger an alert when a time interval between two consecutive overshoots of said gait acceleration threshold value is below the stored time threshold value;
- the storage means store a reference period corresponding to the time threshold value, and in that the calculation means command the emission means to emit the auditory stimulation according to the reference period;
- the calculation means are configured to command the emission means to emit an auditory stimulation from the moment when at least two alert signals are generated within a time interval less than 0.5 seconds, preferably less than 0.3 seconds;
- the device comprises:
  - heart rate measurement means suitable for being worn by the person to measure his or her heart rate; and
  - the storage means store a heart rate threshold value; and the calculation means are configured to generate an alert signal when the measured heart rate has a value above the stored heart rate threshold value;
- the accelerometer is configured to measure an acceleration in another direction different from that of the second direction, and the storage means store a second acceleration threshold value, and the calculation means are configured to inhibit the generation of an alert signal for a predetermined time when an acceleration measured in the other direction has a value above the second stored acceleration threshold value;
- the calculation means are configured to determine, from the acceleration measurements measured by the accelerometer, the orientation of the trunk of the person;
- the storage means store a gait acceleration threshold value and a rest time value, and the calculation means detect a seated or recumbent position of the person wearing the accelerometer when all the acceleration values measured by the accelerometer are below the gait acceleration threshold value for a period greater than the rest time value;
- the calculation means are configured to compare the accelerations measured by the accelerometers periodically, the value of this period being equal to:
  - a first measurement period when the trunk of the person is horizontal; and/or
  - a second measurement period less than the first value, when the trunk of the person is vertical; and
  - a third measurement period less than the second value, when the person is walking.

The invention relates also to a method for calibrating an assistance device as claimed in one of the preceding claims, comprising the steps whereby:
- the accelerometer is arranged on the person,
- a series of acceleration measurements is acquired while the person is walking,
- the parts of the series of acceleration measurements corresponding to an impaired motricity of the person are cut from the series,
- the anticipatory acceleration values and/or an alert acceleration threshold value is determined from the average of the accelerations of the cut series.

Preferably, the gait acceleration threshold value and/or the time threshold value is determined from the average of the accelerations of the cut series.

DESCRIPTION OF THE FIGURES

The invention will be better understood, from the description herein below, which relates to embodiments and variants according to the present invention, given as nonlimiting examples and explained with reference to the attached schematic drawings, in which.

DETAILED DESCRIPTION

Vertical in the present description should be understood to mean a direction parallel to the direction of gravity or at right angles to the plane of the horizon. Horizontal should be understood to mean a direction at right angles to the vertical, therefore at right angles to the direction of gravity. Posture should be understood to mean the position of the body at a given instant, contrary to a movement. A posture is for example the standing position or the seated position.

Figure 1:
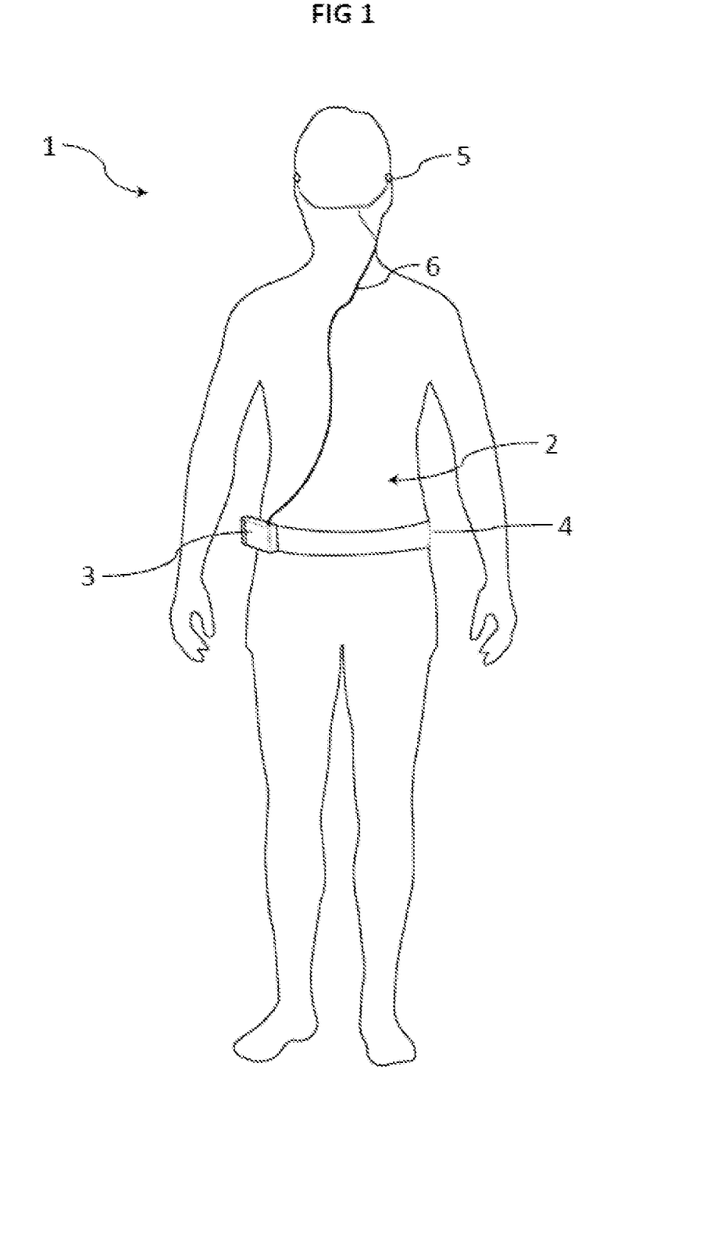
FIG. 1 is a diagram illustrating a person suffering from motor disorders of neurological origin using an assistance device according to a possible embodiment of the invention.

Referring to FIG. 1, an assistance device comprises a housing 3 in which an accelerometer is housed that is suitable for being worn by the person 1 to measure accelerations in at least one direction. Preferably, the accelerometer is suitable for being worn on the trunk 2 of the person. Trunk should be understood to mean the part of the human body ranging from the pelvis to the shoulders. The accelerometer is for example a piezoelectric accelerometer comprising a surface structure of polysilicon suspended above a silicon wafer by a silicon spring exhibiting a resistance to acceleration forces. The deformation of the structure is measured by means of a differential capacitance.

The accelerometer can form part of an inertial unit, comprising, in addition to an accelerometer capable of measuring accelerations in one or more directions, one or more gyrometers capable of measuring angular velocities and/or one or more gyroscopes capable of measuring angular positions. Thus, preferably, the device comprises an inertial unit of which the accelerometer forms part, said inertial unit being configured to determine an orientation of the trunk of the person. As indicated for the accelerometer, the inertial unit is preferably suitable for being worn on the trunk of the person.

The accelerometer is preferably suitable for being worn at the waist level. Thus, in FIG. 1, the person suffering from Parkinson's disease wears a belt 4 around the waist that is provided with the housing 3 comprising this first accelerometer. Preferably, the accelerometer is suitable for measuring accelerations in at least one second direction, different from the first direction, and preferably orthogonal to the first direction. Typically, the accelerometer is capable of determining acceleration measurements in three mutually orthogonal directions, and therefore of reconstructing the acceleration in any direction, as well as the orientation of the accelerometer, and therefore of the trunk 2 of the person 1.

Thus, whether measured directly or reconstructed, the first direction corresponds to the horizontal direction in relation to the person wearing the device. More specifically, the first direction is essentially horizontal, that is to say that the horizontal component of the first direction predominates over the vertical direction.

The motion sensor comprising the accelerometer is suitable for being positioned on the user. The accelerometer can notably be positioned at the level of the trunk, of the hips, of the plexus, or of the lower limbs of the user. Preferably, the motion sensor is positioned so as to be able to measure the accelerations at the level of the hip, of the bust or of the plexus. The motion sensor is thus positioned at the level of one of these parts of the body. In effect, the measurement of the accelerations at these points makes it possible to take account of the movements of both of the two legs, which an accelerometer placed on a foot does not make possible, whereas above the torso, for example on the shoulders, the damping by the body is too significant. Thus, more preferably, the motion sensor is positioned at the level of the crest of ilium of the person 1.

The housing 3 also comprises calculation means, for example a processor or a computer, a microcontroller, a computation unit, or an arithmetic and logic unit, and storage means. The calculation means are connected to the accelerometer, for example by a wireless or wave-based or a wired link, and to the storage means, for example by a physical link. The calculation means and the storage means are typically arranged on the same electronic card, or on several separate cards connected to one another.

The storage means store at least one plurality of prevention acceleration threshold values previously defined for the horizontal direction. These prevention acceleration threshold values are associated with postures of the person, and determined times are associated with each anticipatory acceleration threshold value. More specifically, a determined time associated with an anticipatory acceleration threshold value is a function of the direction of crossing of said anticipatory acceleration threshold value. Thus, for each anticipatory acceleration threshold value, there is a time determined for the crossing from accelerations below said threshold value to accelerations above said threshold value, and a time determined for the crossing from accelerations above said threshold value to accelerations below said threshold value, and these two determined times are different for at least most of the threshold values.

However, in order to implement different functionalities of the device, the storage means can also store other values, and in particular among those are at least an alert acceleration threshold value, a time threshold value, a gait acceleration threshold value and/or a heart rate threshold value.

The device also contains means for emitting an auditory stimulation perceptible to the person wearing the accelerometer. The emission means comprise a transducer 5 suitable for emitting sounds, which can take the form of an earpiece to be placed in the auditory canal of the wearer of the device, or else a transducer suitable for being placed against a temporal bone of the wearer in order to stimulate said bone, such as, for example, an apparatus implementing osteophony. The emission means are linked to the housing 3, and more specifically to the calculation means, by a link 6, which can be wired as in FIG. 1, or else wireless or wave-based.

The device can also comprise a heart rate meter, suitable for measuring the heart rate of the person wearing the device. The latter can be worn when using the device for motricity assistance, or else only when calibrating the latter. The device also comprises at least one battery supplying the various components of the device with electrical energy.

In the assistance device, the calculation means are configured to:
 a) determine a posture of the person from the measured accelerations,
 b) compare the accelerations measured by said accelerometer in the first direction in relation to at least one anticipatory acceleration threshold value associated with said posture;
 c) command the emission of an auditory stimulation as a function of the crossing of said anticipatory acceleration threshold value associated with said posture for a determined time associated with said anticipatory acceleration threshold value.

The device is thus configured to stimulate the wearer of said device when he or she is moving during phases of probability of occurrence of a freezing of gait phenomenon, these phases being determined by the comparison between the measured accelerations and anticipatory acceleration threshold values. More specifically, it involves the comparing of the amplitudes of these accelerations with anticipatory acceleration threshold values.

The probability of this occurrence depends also on the posture of the user. Thus, each anticipatory acceleration threshold value is associated with a posture. Several acceleration threshold values can be associated with one and the same posture. The direction taken into account here is that of the horizontal, and the direction of the accelerations is that of the forward movement of the user.

In order to avoid unnecessarily stimulating the user, the emission of the stimulation is conditional on the crossing of an anticipatory acceleration threshold value for a determined time which is associated with it. Typically, the determined time for which the acceleration must exceed the threshold lies between 150 ms and 2.5 seconds. The determined time for which the acceleration must exceed the threshold depends on the anticipatory acceleration threshold value, which in turn depends on the posture. Consequently, the determined time depends also on the posture. The postures can comprise the seated-recumbent posture and the standing posture. As an example, if the posture of the user is determined as being seated or recumbent, the predetermined time can lie between 200 ms and 1 second. If the posture of the user is determined as being standing, the determined time can lie between 150 ms and 2.5 seconds. This determined time can depend on the direction of crossing, as explained above.

The posture of the person can be determined from the measured accelerations. In addition, or alternatively, it can also be determined from the orientation of the trunk of the user that an inertial unit, worn on this trunk, can determine.

The measurement of the accelerations makes it possible to determine the orientation of the device. It is for example possible to determine the gravity or incorporate the accelerations. Based on the orientation of the device, it is possible to determine the position of the person, and therefore his or her posture in combination with the accelerations. It is therefore possible to determine the posture of the person by the accelerations. For example, it is possible to determine that the person is seated or recumbent if the device is inclined backward, with an inclination threshold exceeded for a certain time (several seconds). Similarly, it is also possible to determine that the person is standing if the position of the device is parallel or at right angles to the ground (depending on the configurations), in a stable manner (over several seconds).

The postures can comprise the seated-recumbent posture and the standing posture. In the case of the seated-recumbent posture, an anticipatory acceleration threshold value associated with the seated-recumbent posture corresponds to a backward imbalance, the auditory stimulation being emitted when the measured accelerations are above said anticipatory acceleration threshold value associated with the seated-recumbent posture corresponding to a backward imbalance. For example, the anticipatory acceleration threshold value associated with the seated-recumbent posture corresponding to a backward imbalance is between $-1.2$ m·s$^{-2}$ and $-1.7$ m·s$^{-2}$, for example $-1.5$ m·s$^{-2}$, and the predetermined time which is associated with it lies between 0.5 and 1 second.

As an example, if the posture of the user is determined as being seated or recumbent, the stimulation is emitted when accelerations greater than $-1.5$ m·s$^{-2}$ in the horizontal direction are measured for at least 0.5 s. In other words, no stimulation is emitted.

In the case of the standing posture, an anticipatory acceleration threshold value associated with the standing posture corresponding to a backward imbalance and an anticipatory acceleration threshold value associated with the standing posture corresponding to a forward movement. The auditory stimulation is emitted when the measured accelerations are below the anticipatory acceleration threshold value associated with the standing posture corresponding to a backward imbalance and when the measured accelerations are above the anticipatory acceleration threshold value associated with the standing posture corresponding to a forward movement.

For example, the anticipatory acceleration threshold value associated with the standing posture corresponding to a backward imbalance is between $-0.8$ m·s$^{-2}$ and $-1.2$ m·s$^{-2}$, for example $-1$ m·s$^{-2}$, and the predetermined time which is associated with it is between 150 and 250 ms, for example 200 ms, and the anticipatory acceleration threshold value associated with the standing posture corresponding to a forward movement is between 2.5 and 3 m·s$^{-2}$, for example 2.8 m·s$^{-2}$, and the predetermined time which is associated with it is between 150 and 250 ms, for example 200 ms.

As an example, if the posture of the user is determined as being standing, the stimulation is emitted when accelerations greater than 2.8 m·s$^{-2}$ are measured for 0.2 s or between $-1.5$ m·s$^{-2}$ and $-1$ m·s$^{-2}$ are measured for 0.2 s. In other words, no stimulation is emitted.

Table 1 below makes it possible to give an example of thresholds used, as a function of the posture determined by the device.

| Posture | Accelerations on the horizontal axis (in m · s$^{-2}$) | | | | |
|---|---|---|---|---|---|
| | −infinity | −1.5 | −1 | 2.8 | +infinity |
| Seated-recumbent | No stimulation | stimulation | | No stimulation | No stimulation |
| Standing | No stimulation | | stimulation | No stimulation | stimulation |

Table 2 below gives examples of predetermined times which can be associated with the acceleration threshold values given in table 1, as a function of the direction of crossing, for different postures determined by the device.

| Posture | Accelerations | Crossing in positive direction | Crossing in negative direction |
|---|---|---|---|
| Seated-recumbent | −1.5 | 350 ms | 500 ms |
| Standing | −1 | 2500 ms | 200 ms |
| | 2.8 | Between 200 and 500 ms | Between 350 and 2500 ms |

"Crossing in positive direction" is used here to denote a crossing of the threshold from accelerations below said threshold value to accelerations above said threshold value, and "crossing in negative direction" is used to denote a crossing from accelerations above said threshold value to accelerations below said threshold value.

When the stimulation conditions are satisfied, the calculation means command the emission means to emit the auditory stimulation according to a reference period corresponding to a calculated frequency of the steps of the person. The auditory stimulation comprises a rhythmic pulsing, which can be isolated and correspond for example to a repetition of a short sound, or even be coupled to other sounds, as in the case of a melody. In all cases, the rhythmic pulsing is easily identified by the user. The period of the pulsing of the auditory stimulation is based on a reference period stored in the storage means. The period of the pulsing is calculated as a function of the average period of the steps when the person is walking without exhibiting freezing of gait. It therefore varies according to the individual. As an example, when the person walks with an average of 140 steps per minute, that amounts to a period of approximately 0.43 seconds between each step. The period of the pulsing of the auditory stimulation is then 0.43 seconds.

The auditory stimulation can be emitted, depending on the case, as long as the conditions of emission thereof are fulfilled, be followed by a certain time even after these conditions have ceased to be fulfilled and/or be stopped after a determined time even when the conditions are fulfilled. For example, in the context of the backward imbalance, the auditory stimulation can be emitted as long as the measured accelerations lie between $-1.5$ m·s$^{-2}$ and $-1$ m·s$^{-2}$. In the case of forward movement, the stimulation can be continued for 40 to 50 seconds when the corresponding acceleration threshold is crossed (for example the threshold of 2.8 m·s$^{-2}$).

Preferably, the storage means store at least one alert acceleration threshold value, and the accelerometer is also suitable for measuring accelerations in a second direction, said second direction corresponding to the vertical.

In the assistance device, the calculation means are then also configured to perform the following steps:
a) comparing the accelerations measured in the second direction in relation to the alert acceleration threshold value;
b) generating an alert signal when a measured acceleration has a value above the alert acceleration threshold value.

In effect, at the start of a freezing of gait, the person suffering from Parkinson's disease exhibits a gait that is disharmonious and asymmetrical from the anatomo-functional point of view. The steps become shorter, closer together, and faster. This is reflected, in measured vertical acceleration terms, in greater acceleration amplitudes, which then consequently exceed an alert acceleration threshold value, and therefore trigger the generation of an alert signal. The alert acceleration threshold value is parameterized according to each person, but typically lies, as an absolute value, between 1 and 7 m·s$^{-2}$, more specifically between 2 and 6 m·s$^{-2}$, and even more specifically between 3 and 5 m·s$^{-2}$. It is thus possible to detect, as quickly as possible, the occurrence of a freezing of gait episode. Then, the calculation means are configured to command the emission means to emit an auditory stimulation as a function of the alert signal.

However, the triggering of an alert signal each time an alert acceleration threshold value is crossed results in many unwanted triggerings. In effect, a strong acceleration can be caused not only by a freezing of gait, but also by other factors, for example when the foot strikes an obstacle.

Thus, preferably, the calculation means are configured to command the emission means to emit an auditory stimulation from the moment when at least two alert signals are generated within a time interval less than 0.5 seconds, preferably less than 0.3 seconds. Consequently, an isolated overshoot of the alert acceleration threshold value does not result in the generation of an auditory stimulation.

Nevertheless, even with the demand for the temporal proximity of two threshold overshoots, there can be false alerts resulting in an unwanted triggering of the auditory stimulation. The detection of a closer frequency of the steps is therefore used. For this, the storage means store a time threshold value and a gait acceleration threshold value, and the calculation means are configured to measure a time interval between two acceleration measurements exceeding said gait acceleration threshold value and trigger an alert when a time interval between two consecutive overshoots of said gait acceleration threshold value is below the stored time threshold value.

The gait acceleration threshold value is lower than the alert acceleration threshold value. For example, it is lower, as an absolute value, than 3 m·s$^{-2}$. The overshoot in amplitude of the gait acceleration threshold value by the measured accelerations corresponds to the detection of a step. The time interval between two consecutive overshoots therefore corresponds to the time interval between two steps. Upon a freezing of gait episode, the time interval between the steps decreases. The first criterion of overshoot of the alert acceleration threshold therefore has added to it a second criterion relating to the frequency of the steps. That makes it possible to better detect the episodes that really correspond to a freezing of gait.

Moreover, strong accelerations can be detected in the absence of freezing of gait, in particular when the person changes position, for example when he or she climbs a staircase.

In this case, it is best to detect this situation as not corresponding to the gait. To this end, the accelerometer is adapted to measure an acceleration in another direction different from the second direction, and preferably at right angles thereto; and the storage means store a second acceleration threshold value. The calculation means can then be configured to inhibit the generation of an alert signal for a predetermined time when a measured acceleration has a value above this second alert acceleration threshold value.

More generally, the calculation means are configured to detect, from the measurements of the accelerometer, and/or possibly through those of a gyrometer or gyroscope, the position of the body and the situation of movement or of rest of the person wearing said accelerometer. The position of the body can be determined by means of the detection of the acceleration of the Earth's gravity, which indicates the vertical, or else directly by the gyroscope. The storage means store a gait acceleration threshold value, and the calculation means detect a position of rest of the person wearing the accelerometers when all the values measured by the accelerometers are below the gait threshold value for a time greater than a predetermined time.

Thus, when the person is detected as being standing, he or she is considered to be at rest when only accelerations lying within an acceleration interval, such as $-1$ m·s$^{-2}$ and 2.8 m·s$^{-2}$ in the vertical direction, are measured for a time interval such as 2.5 s. When the person is detected as being seated or recumbent, he or she is considered to be resting when only accelerations lying within an acceleration interval, such as between $-1.5$ m·s$^{-2}$ and 1.5 m·s$^{-2}$ in the vertical direction, are measured for a time interval such as 0.35 s.

The calculation means are configured to compare the accelerations measured by the accelerometer periodically, the value of this period being equal to:

a first measurement period when the trunk of the person is non-vertical, that is to say when he or she is recumbent; and/or a second measurement period below the first value, when the trunk of the person is vertical, that is to say when he or she is seated; and a third measurement period below the second value, when the person is walking.

For example, the first measurement period is greater than 75 ms, and is for example 100 ms, whereas the second measurement period lies between 75 ms and 25 ms, and is for example 50 ms, and the third measurement period is less than 25 ms, and is for example 10 ms.

The auditory stimulation emitted upon the detection of the occurrence of a freezing of gait episode is preferably the same as in prevention of the freezing of gait, and the period of the pulsing of the auditory stimulation is based on a reference period stored in the storage means, linked to the time value used to detect an excessively fast frequency of the steps. The period of the pulsing is calculated as a function of the average period of the steps when the person is walking without exhibiting freezing of gait.

The auditory stimulation can be emitted upon the detection of the freezing of gait, using alert signals described previously, or be emitted on expiration of a time delay which follows the detection of the freezing of gait. This time delay can lie between 0.1 and 37 seconds for example, but, when present, it can be at least 2 seconds, for example 10 seconds. Prior to the time delay, a stop signal is emitted by the emission means, indicating to the person to stop. That makes it possible to bring the person back to a motricity that he or she controls, that is to say immobility, then restart using the auditory stimulation following the time delay.

However, the stopping of the person can result in falls, because he or she may be unbalanced upon the freezing of gait. Moreover, the duration of the time delay commensurately slows down the movements of the person. Thus, the auditory stimulation is preferably sent without time delay, or with a very short time delay, less than a tenth of a second.

Moreover, it is commonplace, upon freezing of gait, for the heart rate of the person to increase, and suddenly become greater than a normal walking heart rate of that person. This higher heart rate can be used to distinguish a freezing of gait from other cases that can possibly lead to similar accelerations. To this end, the device can comprise heart rate measurement means suitable for being worn by the person to measure his or her heart rate. The storage means then store a heart rate threshold value and the calculation means are configured to generate an alert signal when the measured heart rate has a value above the stored heart rate threshold value, the latter corresponding to a normal walking heart rate of that person, previously determined.

Figure 2:
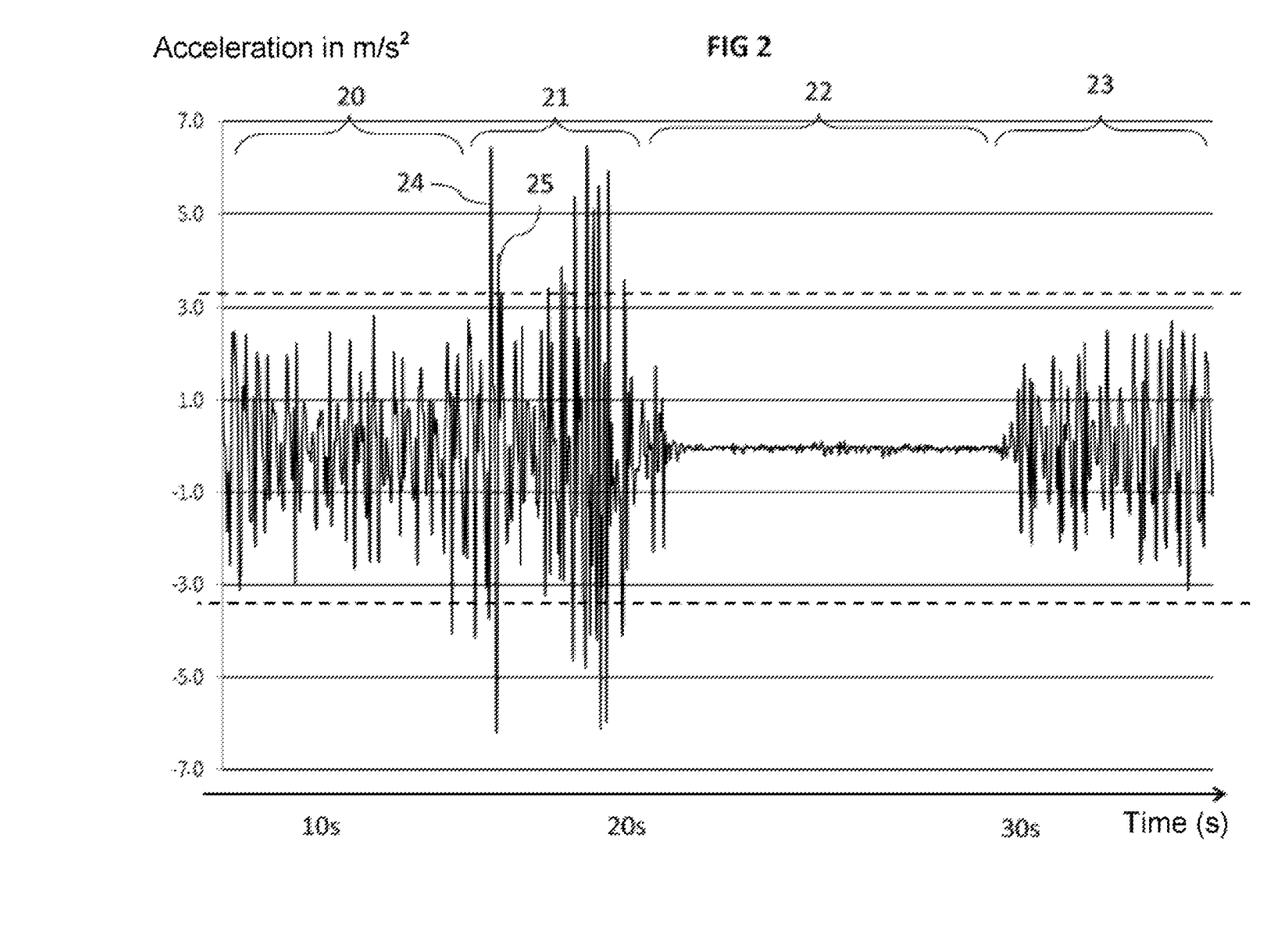
FIG. 2 is a diagram illustrating the accelerations in the vertical direction measured by an accelerometer showing a freezing of gait.

FIG. 2 illustrates the accelerations measured in the vertical direction for a person suffering from Parkinson's disease when walking and suddenly experiencing a freezing of gait.

In a first part 20, the person walks without exhibiting freezing of gait. The measured accelerations are below an alert acceleration threshold represented by the dashed horizontal lines, above for the positive values and below for the negative values. Furthermore, the acceleration peaks which exceed the gait acceleration threshold value are spaced apart by a time interval above the time threshold value.

A calibration of the assistance device is implemented to adapt to the person wearing the device the different values used in the context of the use of the device, such as the alert acceleration threshold value.

In a second part 21, a freezing of gait occurs. The amplitudes of the accelerations are greater, and exceed the alert acceleration threshold value. Furthermore, the acceleration peaks which exceed the gait acceleration threshold value become closer together: the time intervals spacing them apart are below the time threshold value.

The two first overshoots 24, 25 of the alert acceleration threshold value occur within a time interval less than a few tenths of a second. The calculation means then command the emission means to emit the auditory stimulation after a time delay of 10 seconds. During this 10 second time delay, the person experiencing the freezing of gait is stopped, which corresponds to the almost zero acceleration values of the part 22. A stop sound can be emitted to indicate to the person to stop, which prevents him or her from falling. It is also possible to emit the auditory stimulation upon the detection of the freezing of gait, without time delay.

Here, the audible signal is emitted from the $30^{th}$ second. The fourth part 23 thus corresponds to the resumption of walking by the person listening to the auditory stimulation. It can be seen that the acceleration peaks are evenly spaced apart with regular amplitudes, thus indicating the resumption of a regular and harmonious gait.

In the context of this calibration method, the accelerometer is arranged on the person, notably at his or her belt level, that is to say at the level of the crest of the ilium, as illustrated in FIG. 1. As previously, the accelerometer can be arranged at the level of the trunk, of the hips, of the plexus, or of the lower limbs. The person then walks, and at least one series of acceleration measurements is acquired while the person is walking, by means of the accelerometer.

These acceleration measurements are used to determine the parameters (amplitude of the accelerations, rate, etc.) of a normal gait of the person, that is to say in the absence of a freezing of gait episode. To this end, the parts corresponding to an impaired motricity of the person, that is to say the parts corresponding to freezing of gait episodes, and more generally to a non-normal gait, are cut from the series of acceleration measurements. This selection in the series of acceleration measurements can be done manually by a professional observing the gait of the patient, in as much as a freezing of gait episode can be identified clearly by a professional. This selection can also be based on the observation of measurements, since, as in FIG. 2, the parts corresponding to a normal gait and the parts corresponding to a freezing of gait or to a stop are easily identifiable.

Then, from the duly cut series, it is possible to determine the parameters of a normal gait. In particular, a calculation on the data of the accelerations makes it possible to determine the alert acceleration threshold beyond which the measured acceleration is considered abnormal and possibly indicating the occurrence of a freezing of gait. The calculation on the data of the accelerations to determine the alert acceleration threshold can for example involve statistical concepts such as the average of the amplitudes of the accelerations and their standard deviation.

The alert acceleration threshold can be evolutive, with a first determination by means of a first series of samples extracted from the cut series, then a confirmation or a modification of this threshold by means of other series of samples, extracted from the same cut series or from another cut series obtained from the same person.

The gait acceleration threshold value can also be determined from the average of the accelerations. The time threshold value can also be determined from the cut series, by detecting the acceleration peaks corresponding to a step and by thus determining the rate of the gait.

Moreover, when walking while the series of accelerations is recorded, the person preferably wears a heart rate meter, and his or her heart rate is measured at the same time as the acceleration. This heart rate can be used to retain only the parts of the series corresponding to a normal gait: the parts associated with a heart rate higher than the average while he or she is walking are discarded. In effect, these parts can indicate not only the occurrence of a freezing of gait, but also other stress events which could result in an abnormal gait.

Moreover, whether for the implementation of the calibration method or for a tracking of the person wearing the device while it is being used, the computation means are preferably configured to store, on the storage means, the measurements performed by at least one by at least one measurement device of the assistance device, such as the accelerometer and/or the heart rate meter. It is then possible to proceed with periodic recalibrations of the device based on the measurements recorded by the latter during the use of the device, and stored in the storage means. It is thus possible to provide a recalibration periodicity of between several times a day and once a week.

The invention is not limited to the embodiment described and represented in the attached figures. Modifications are still possible, particularly from the point of view of the construction of the various elements or by the substitution of technical equivalents, without departing in any way from the scope of protection of the invention.

The invention claimed is:

1. A method for preventing freezing of gait and restoring a normal gait in a person suffering from a motor disorder of neurological origin, comprising:
   measuring accelerations of said person in a vertical direction;
   comparing the accelerations measured in the vertical direction to at least one alert acceleration threshold value,
   generating an alert signal when a measured acceleration has a value above the alert acceleration threshold value; and
   emitting an auditory stimulation as a function of the alert signal, wherein the auditory stimulation comprises a rhythmic pulsing.

2. The method of claim 1, further comprising measuring a time interval between two acceleration measurements that exceed a gait acceleration threshold value and triggering an alert when a time interval between two consecutive overshoots of said gait acceleration threshold value is below the stored time threshold value.

3. The method of claim 1, further comprising emitting the auditory stimulation according a reference period, said reference period corresponds to a calculated frequency of the steps of the person.

4. The method of claim 1, wherein the rhythmic pulsing is calculated as a function of the average period of the steps when the person is walking without exhibiting freezing of gait.

5. The method of claim 1, wherein the auditory stimulation is emitted from when at least two alert signals are generated within a time interval less than 0.5 seconds.

6. The method of claim 1, wherein the auditory stimulation is emitted from when at least two alert signals are generated within a time interval less than 0.3 seconds.

7. The method of claim 1, wherein the alert acceleration threshold value is between 1 and 7 $m \cdot s^{-2}$.

8. The method of claim 1, wherein the alert acceleration threshold value is between 3 and 5 $m \cdot s^{-2}$.

9. The method of claim 1, wherein the person suffers from Parkinson's disease.

10. The method of claim 1, further comprising measuring said person's heart rate and generating an alert signal when the measured heart rate has a value above a stored heart rate threshold value.

11. The method of claim 1, further comprising measuring an acceleration in another direction different from that of the vertical direction, and inhibiting the generation of an alert signal for a predetermined time when an acceleration measured in said another direction has a value above a second acceleration threshold value.

12. The method of claim 1, further comprising detecting a seated or recumbent position of the person when all the acceleration values measured are below the gait acceleration threshold value for a period greater than a rest time value.

13. The method of claim 1, further comprising
   measuring accelerations of said person in a horizontal direction;
   comparing the accelerations measured by said accelerometer in the first direction in relation to at least one anticipatory acceleration threshold value associated with said posture;
   comparing the accelerations measured in the horizontal direction to at least one anticipatory acceleration threshold value associated with the person's posture; and
   emitting an auditory stimulation as a function of crossing said anticipatory acceleration threshold value associated with said posture for a predetermined time associated with said anticipatory acceleration threshold value.

14. The method of claim 1, wherein the emitting of an auditory stimulation is performed by an earpiece placed in the auditory canal of the person, or a transducer suitable for being placed against a temporal bone of the person in order to stimulate said bone.

15. The method of claim: 14, wherein the transducer is an apparatus implementing osteophony.

* * * * *